United States Patent
Yim et al.

(10) Patent No.: US 11,617,882 B2
(45) Date of Patent: Apr. 4, 2023

(54) APPARATUS FOR INSERTION OF NERVE ELECTRODE STRUCTURE

(71) Applicants: KOREA INSTITUTE OF SCIENCE AND TECHNOLOGY, Seoul (KR); RESEARCH & BUSINESS FOUNDATION SUNGKYUNKWAN UNIVERSITY, Suwon-si (KR)

(72) Inventors: Sehyuk Yim, Seoul (KR); Donghyun Hwang, Seoul (KR); Yong Seok Ihn, Seoul (KR); Keehoon Kim, Seoul (KR); Sang Rok Oh, Seoul (KR); Jinwoo Jeong, Suwon-si (KR)

(73) Assignees: Korea Institute of Science and Technology, Seoul (KR); Research & Business Foundation Sungkyunkwan University, Suwon-si (KR)

( * ) Notice: Subject to any disclaimer, the term of this patent is extended or adjusted under 35 U.S.C. 154(b) by 119 days.

(21) Appl. No.: 16/662,102

(22) Filed: Oct. 24, 2019

(65) Prior Publication Data
US 2021/0121688 A1    Apr. 29, 2021

(51) Int. Cl.
*A61N 1/05* (2006.01)
(52) U.S. Cl.
CPC ......... *A61N 1/0558* (2013.01); *A61N 1/0556* (2013.01)
(58) Field of Classification Search
CPC .............. A61N 1/0558; A61N 1/0556; A61N 2001/0582
See application file for complete search history.

(56) References Cited

U.S. PATENT DOCUMENTS 4,177,818 A * 12/1979 De Pedro ............. A61N 1/0587
607/130
5,361,760 A   11/1994 Normann et al.
(Continued)

FOREIGN PATENT DOCUMENTS

KR   10-2012-0010221 A   2/2012
KR      10-1808254 B1   12/2017
(Continued)

OTHER PUBLICATIONS

Almut Branner et al., "Long-Term Stimulation and Recording With a Penetrating Microelectrode Array in Cat Sciatic Nerve", IEEE Transactions on Biomedical Engineering, Jan. 2004, pp. 146-157, vol. 51, No. 1.

(Continued)

*Primary Examiner* — Michael W Kahelin
(74) *Attorney, Agent, or Firm* — Rabin & Berdo, P.C.

(57) ABSTRACT

A nerve cover for covering a nerve within a living body tissue to protect the nerve includes a base of a flat plate shape, and a pair of covers protruding upward the base to form a hole for receiving a nerve, with one end attached to the base and the other end spaced apart from the one end, wherein when the base is bent in an arch shape when viewed from a side, a spacing between the pair of covers is expanded. In addition, an apparatus for insertion of an electrode structure includes a nerve cover fixing part which fixes the nerve cover with the base being bent, and an electrode structure fixing part in which the electrode structure is mounted, and which linearly moves the mounted electrode structure in an insertion direction to insert the electrode structure into the nerve surrounded by the nerve cover.

11 Claims, 10 Drawing Sheets

(56) References Cited

U.S. PATENT DOCUMENTS

| | | | |
|---|---|---|---|
| 6,304,785 B1 | 10/2001 | McCreery et al. | |
| 8,226,661 B2 | 7/2012 | Balling et al. | |
| 2006/0247682 A1* | 11/2006 | Gerber | A61B 5/4393 607/2 |
| 2007/0073098 A1* | 3/2007 | Lenker | A61B 17/12009 600/30 |
| 2010/0145222 A1* | 6/2010 | Brunnett | A61B 5/05 600/554 |
| 2010/0168831 A1* | 7/2010 | Korivi | A61N 1/0556 264/134 |
| 2016/0310729 A1* | 10/2016 | Ramesh | A61N 1/3752 |
| 2018/0104478 A1* | 4/2018 | Hwang | A61N 1/0551 |
| 2018/0125427 A1 | 5/2018 | Oh et al. | |
| 2019/0060638 A1* | 2/2019 | Oh | A61B 17/3468 |

FOREIGN PATENT DOCUMENTS

| | | |
|---|---|---|
| KR | 101842618 B1 | 3/2018 |
| KR | 1020180052194 A | 5/2018 |
| WO | WO 2010/077494 A2 | 7/2010 |

OTHER PUBLICATIONS

Sehyun Yim et al., "Handheld Nerve Electrode Insertion Tool", IEEE/ASME Transactions on Mechatronics, Oct. 2018, pp. 2525-2530, vol. 23, No. 5.

* cited by examiner

APPARATUS FOR INSERTION OF NERVE ELECTRODE STRUCTURE

BACKGROUND

1. Field

The present disclosure relates to an apparatus for insertion of a nerve electrode structure, and more particularly, to an apparatus for insertion of an electrode structure to fix a nerve cover to easily cover a peripheral nerve and to insert and fix an electrode structure into the nerve surrounded by the nerve cover.

Explanation of National-Supported Research and Development

This study was supported by STEAM research project of the Ministry of Science and ICT (Integration and demonstration of a bionic arm system having biosignal-based controlling function, Project No. 1711058885) under the superintendence of National Research Foundation of Korea.

2. Description of the Related Art

Many studies for defining neural activity by stimulating nerves or acquiring and analyzing neural signals have been made to date. Particularly, technologies that measure biosignals in the brain and nerves or deliver stimuli using ultra micro nerve electrodes are widely used in the field of biotechnology, biomedical engineering and neuroscience.

Among various invasive nerve electrodes, a three-dimensional multielectrode array (MEA) has been long used in experiments and its performance has been proved, and such a research requires a process of inserting a probe electrode into a desired location of a nerve.

Because nerves such as peripheral nerves are usually surrounded by the tough and strong outer covering, an auxiliary instrument is needed to insert an electrode into a nerve. The existing apparatus for insertion of an electrode structure involves a process in which a user shoots an electrode structure using air pressure and fixes it into a nerve, and then covers the nerve and the electrode structure with a biocompatible material, followed by suturing.

In the case of the existing apparatus for insertion of an electrode structure by air pressure, insertion is accompanied by strong impacts, causing damage to the nerve or the electrode structure. Additionally, the existing apparatus has a very high price, and a process of suturing the electrode cover while paying attention to prevent the electrode structure from slipping requires a high level of concentration and a long operation time as well. By this reason, experiments greatly rely on physicians' skill level, and it is difficult to maintain the consistency and reliability of experimental results.

RELATED LITERATURES

Patent Literatures (Patent Literature 1) U.S. Pat. No. 5,361,760 (1994 Nov. 8)

SUMMARY

The present disclosure is designed to solve the above-described problem, and therefore the present disclosure is directed to providing an apparatus for insertion of an electrode structure for easily inserting and stably fixing an electrode structure into a nerve.

To achieve the above-described object, according to an aspect of the present disclosure, there is provided a nerve cover for covering a nerve within a living body tissue to protect the nerve, the nerve cover including a base of a flat plate shape, and a pair of covers protruding upward the base to form a hole for receiving a nerve, with one end attached to the base and the other end spaced apart from the one end, wherein when the base is bent in an arch shape when viewed from a side, a spacing between the pair of covers is expanded.

According to an embodiment of the present disclosure, the base may include one or more fixing holes that are sutured with a string to fix the nerve cover to the living body tissue.

According to another aspect of the present disclosure, there is provided an apparatus for insertion of an electrode structure for inserting an electrode structure into a nerve within a living body tissue, including a nerve cover fixing part which fixes the nerve cover with the base being bent in an arch shape when viewed from the side and the spacing between the pair of covers being expanded, and an electrode structure fixing part in which the electrode structure is mounted, and which linearly moves the mounted electrode structure in an insertion direction to insert the electrode structure into the nerve surrounded by the nerve cover.

According to an embodiment of the present disclosure, the apparatus for insertion of an electrode structure may further include a pressing part which applies a force to the electrode structure fixing part to move the electrode structure in the insertion direction.

According to an embodiment of the present disclosure, the electrode structure fixing part may be connected with the pressing part by a central pole, and the force applied to the pressing part may be transferred to the electrode structure fixing part through the center pole.

According to an embodiment of the present disclosure, the apparatus for insertion of an electrode structure may further include an elastic element disposed between an elastic press plate attached to the center pole and a support through which the center pole moves, wherein the elastic element is compressed against the support as the center pole moves when a force above a threshold is applied to the pressing part.

According to an embodiment of the present disclosure, the electrode structure fixing part may include a magnetic element inside, and the electrode structure may include a magnetic element on top, and may be fixed to the electrode structure fixing part by a magnetic force between the magnetic elements.

According to an embodiment of the present disclosure, the electrode structure may be fixed to the electrode structure fixing part by a negative pressure, and when the negative pressure is removed, may be separated from the electrode structure fixing part.

According to an embodiment of the present disclosure, the nerve cover may be made of a soft material having an elastic property, and while the electrode structure is inserted into the nerve surrounded by the nerve cover through the linear movement, the base bent into the arch shape may be restored to a flat shape and the expanded spacing between the pair of covers may be restored to an original spacing.

According to an embodiment of the present disclosure, the apparatus for insertion of an electrode structure may further include a high frequency vibration motor attached to the pressing part or the electrode structure fixing part, wherein the high frequency vibration motor reduces a pressure and friction applied to the living body tissue while the electrode structure is inserted into the nerve.

The apparatus according to various embodiments of the present disclosure fixes the nerve cover to facilitate the insertion of the nerve, and allows the electrode structure to be inserted into the nerve stably and effectively. Additionally, the proposed apparatus can insert the electrode structure into the nerve surrounded by the nerve cover quickly, precisely and conveniently, and stably fix the nerve—the cover—the electrode structure to one another using friction with electrode probes penetrating the nerve cover. The nerve cover according to various embodiments of the present disclosure provides a structure that covers the nerve to protect the nerve from external impacts and is easy to be fixed to the nerve.

The effects that can be obtained from the present disclosure are not limited to the above mentioned effects, and other effects not mentioned herein will be clearly understood by those having skill in the technical field pertaining to the present disclosure from the following disclosure.

DETAILED DESCRIPTION

Hereinafter, exemplary embodiments of the present disclosure will be described with reference to the accompanying drawings. The present disclosure is described with reference to the embodiments shown in the drawings, but this is described as an embodiment, and the technical spirit of the present disclosure and its key elements and operation are not limited thereto.

Figure 1:
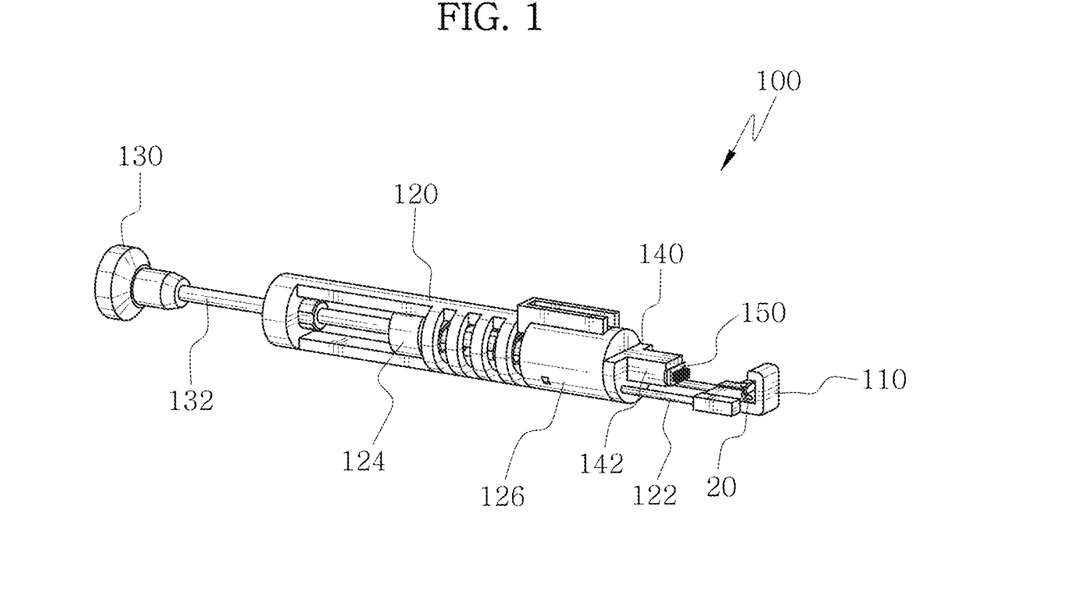
FIG. 1 is a perspective view of an apparatus for insertion of an electrode structure according to an embodiment of the present disclosure.
Figure 2:
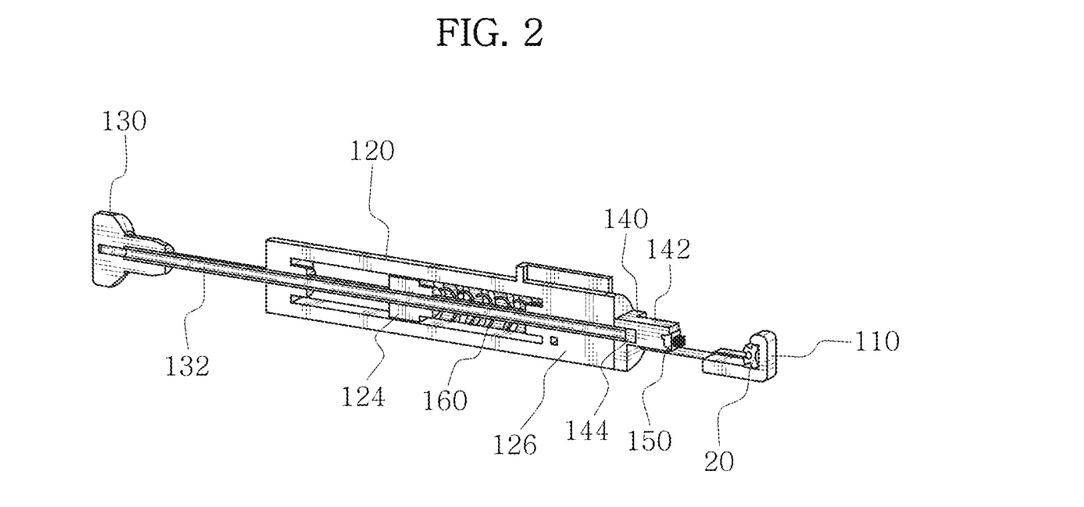
FIG. 2 is a vertical cross-sectional view of the apparatus for insertion of an electrode structure of FIG. 1 according to an embodiment of the present disclosure.

FIGS. 1 and 2 are a perspective view and a vertical cross-sectional view of an apparatus 100 for insertion of an electrode structure according to an embodiment of the present disclosure, respectively. For example, the electrode structure may be a three-dimensional multielectrode array (e.g., Utah electrode array).

Referring to FIGS. 1 and 2, an apparatus 100 for insertion of an electrode structure according to an embodiment of the present disclosure includes a nerve cover fixing part 110, a body 120, a pressing part 130 and an electrode structure fixing part 140.

The nerve cover fixing part 110 has a structure that is easy to insert a nerve 10 into a hole 23 of a nerve cover 20 and is formed with a structure that fixes the nerve cover 20. For example, in the nerve cover 20 of a structure shown in FIG. 3, the entrance size of the hole 23 is much smaller than the diameter of the nerve 10, which makes it difficult to easily insert the nerve 10 into the hole 23. In this instance, when a base 24 of a flat bottom plate of the nerve cover 20 made of a material having an elastic property is bent into an arch shape when viewed from the side and fixed to the nerve cover fixing part 110, the entrance size of the hole 23 is expanded more than the diameter of the nerve 10, facilitating the insertion of the nerve 10. According to an embodiment of the present disclosure, the nerve cover fixing part 110 may further include a groove structure to insert and fix the nerve cover 20.

The body 120 includes a center pole 132 inside, and is provided with the nerve cover fixing part 110 and the electrode structure fixing part 140. The body 120 is connected with one end of a sliding element 122, and the other end of the sliding element 122 is connected with the nerve cover fixing part 110. As described below, when a predetermined force is applied to the pressing part 130, the electrode structure fixing part 140 connected to the end of the center pole 132 moves toward the nerve cover fixing part 110 along the sliding element 122. Through this movement, the electrode structure fixing part 140 may be disposed in proximity to the nerve cover fixing part 110 where the nerve is disposed, and an electrode structure 150 may be inserted and stably fixed into the nerve cover 20 fixed to the nerve cover fixing part 110 and a target insertion location of the nerve 10 surrounded by the nerve cover 20.

The body 120 may have a shape that at least part of the body 120 is open along the movement path of the center pole 132. According to an embodiment of the present disclosure, the body 120 may be connected with a fixing part body 142 of the electrode structure fixing part 140.

The pressing part 130 is connected with the center pole 132 and moves the electrode structure fixing part 140. According to an embodiment of the present disclosure, when a force above the threshold is applied to the pressing part 130, the pressing part 130 moves the electrode structure fixing part 140 so that the electrode structure 150 mounted at one end of the electrode structure fixing part 140 may be inserted into the nerve positioned in the nerve cover fixing part 110.

According to an embodiment of the present disclosure, in the case of the apparatus 100 for insertion of an electrode structure of a type of fixing the electrode structure 150 by the negative pressure, the electrode structure fixing part 140 may be connected to a suction pump through the pressing part 130. The pressing part 130 and the center pole connected to the pressing part 130 are hollow inside, and the electrode structure 150 may be fixed to the end of the electrode structure fixing part 140 using the negative pressure by the suction pump connected through the hole of the pressing part 130. After the electrode structure 150 is inserted into the nerve, the negative pressure may be removed, thereby easily separating the electrode structure 150 from the apparatus 100 for insertion of an electrode structure.

According to another embodiment of the present disclosure, in the case of the apparatus 100 for insertion of an electrode structure of a type of fixing the electrode structure 150 by the magnetic force, as described below, the electrode structure 150 may be fixed to the end of the electrode structure fixing part 140 by a weak magnetic force, and after it is inserted into the nerve, the electrode structure 150 may be easily separated from the apparatus 100 for insertion of an electrode structure by friction with the nerve cover 20.

The electrode structure fixing part 140 is connected with the pressing part 130 through the center pole 132. The electrode structure fixing part 140 moves toward the nerve by the force applied to the pressing part 130, and through this, the electrode structure 150 may be inserted into the nerve cover 20 fixed to the nerve cover fixing part 110 and a target part of the nerve 10 surrounded by the nerve cover 20. To accurately insert the electrode structure 150 into the target part of the nerve 10 only by the linear movement of the electrode structure fixing part 140, the electrode structure fixing part 140 and the nerve cover fixing part 110 may be placed on the same axis. The electrode structure 150 may be fixed to the end of the electrode structure fixing part 140 by the negative pressure, and after it is inserted into the nerve, may be separated by removing the negative pressure, or may be loaded at the end of the electrode structure fixing part 140 by the magnetic force.

As shown in FIG. 1, the apparatus 100 for insertion of an electrode structure may further include an elastic element 160.

The elastic element 160 is fixed and disposed between a support 126 and an elastic press plate 124. The support 126 may be integrally formed with the body 120 or may be connected to the body 120. The elastic press plate 124 is attached to one point disposed in the body 120 of the center pole 132 connected to the pressing part 130, and the center pole 132 may move the connected electrode structure fixing part 140 while moving through an inner hole of the support 126 disposed at the end of the body 120. When a predetermined magnitude of force is applied to the pressing part 130, the force is transferred to the elastic press plate 124 fixed and attached to the center pole 132, and the elastic element 160 is compressed against the support 126 by the force transferred to the elastic press plate 124. That is, when the force above the threshold is applied, the elastic element 160 is compressed against the support 126 by the elastic press plate 124, and the electrode structure fixing part 140 connected to the center pole 132 linearly moves toward the nerve cover fixing part 110. Through this, as shown in FIGS. 6B to 6D, the electrode structure fixing part 140 having the loaded electrode structure 150 may be stably inserted into the nerve 10 surrounded by the nerve cover 20 fixed to the nerve cover fixing part 110.

According to an embodiment of the present disclosure, the elastic element 160 may be a spring, but the present disclosure is not limited to this example, and any known elastic structure may be used as the elastic element.

According to an embodiment of the present disclosure, the apparatus 100 for insertion of an electrode structure may further include a high frequency vibration motor (not shown), and through the high frequency vibration motor, it is possible to reduce the pressure and friction applied to the living body tissue when the probes of the electrode structure are inserted into the nerve. For example, the high frequency vibration motor may be attached to the pressing part 130 or the electrode structure fixing part 140 to apply high frequency vibration to the probes of the electrode structure.

To stably fix the electrode structure into the nerve, a surgical procedure has been used, in which the electrode structure is inserted into the nerve using a pneumatic inserter, and the nerve and the electrode structure are covered with a material having good biocompatibility (e.g., a soft tube) and sutured. This surgical procedure using the existing apparatus is complex, and even affects the experimental results depending on the physicians' skill level, which makes it difficult to obtain consistent and reliable results.

In contrast, the proposed apparatus 100 for insertion of an electrode structure provides a simple and convenient structure in which the nerve cover 20 is fixed to the nerve cover fixing part 110 to make it easy to insert the nerve 10, the nerve 10 is positioned in the hole 23 of the nerve cover 20, and the electrode structure 150 is inserted into the nerve cover 20 and the nerve 10 surrounded by the nerve cover 20 at the same time. Through the apparatus 100 for insertion of an electrode structure, it is possible to fix the electrode structure 150 to the nerve 10 surrounded by the nerve cover 20 in a simple and convenient manner without damage to the nerve, and stably fix the electrode structure using a larger friction between the electrode probes 152 and the nerve cover 20 than friction between the nerve 10 and the electrode probes 152.

Hereinafter, through FIGS. 3 to 6E, the structure of the nerve cover 20 according to an embodiment of the present disclosure and the process of inserting the electrode structure 150 into the nerve 10 after covering the nerve 10 with the nerve cover 20 using the apparatus 100 for insertion of an electrode structure is specifically shown.

Figure 3:
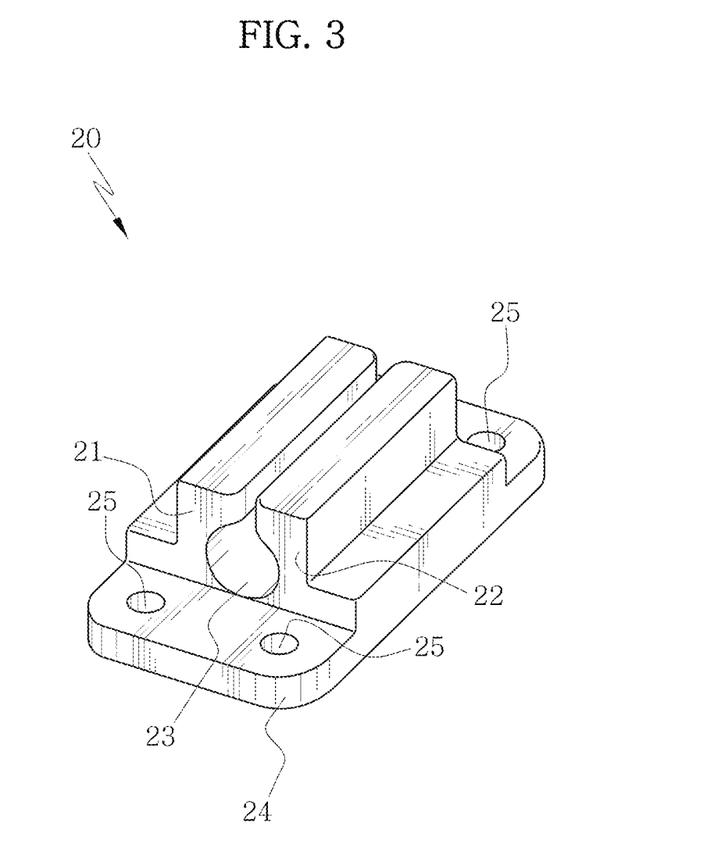
FIG. 3 is a perspective view of a nerve cover according to an embodiment of the present disclosure.

FIG. 3 is a perspective view of the nerve cover 20 according to an embodiment of the present disclosure.

Referring to FIG. 3, the nerve cover 20 includes a base 24, a pair of covers 21, 22 and a hole 23 formed by the pair of covers 21, 22 facing each other. According to an embodiment of the present disclosure, the nerve cover 20 may be made of a polymer or silicone material that has an elastic property and is soft, but may be made of any soft material that can cover the nerve inside to prevent the nerve from being damaged and restore to the original shape after the shape changes.

The base 24 is in the shape of a thin and wide plate. On the base 24, the pair of covers 21, 22 may protrude and be attached with their ends extending inward such that they face each other, forming the hole 23. The hole 23 provides a space for receiving the nerve 10, and may have a circular cross section with an open entrance on the opposite side to a surface attached to the base 24. The base 24 and the pair of covers 21, 22 may be separately formed and then combined together, and may be integrally formed. According to the property of the elastic material, the base 24 may be bent into an arch shape to expand the entrance of the hole 23, and the bent base 24 may be fixed to the nerve cover fixing part 110, forming a structure in which the nerve 10 can be easily inserted into the hole 23. When the nerve 10 is inserted into the hole 23 and the pressure is applied down to the base 24, the shape may be easily restored, and through this, the electrode structure 150 may be stably inserted after the nerve cover 20 easily covers the nerve 10.

According to an embodiment of the present disclosure, the nerve cover 20 may further include one or more fixing holes 25. After the nerve cover 20 covers the nerve 10 and the electrode structure 150 is inserted and fixed into the nerve 10 through the nerve cover 20, the position of the complex structure of the nerve—the nerve cover—the electrode structure may be fixed more stably by suturing with the surrounding tissues or muscles using a string inserted into the fixing holes 25 of the nerve cover 20. For example, the nerve cover 20 may include four fixing holes 25 near the four corners of the base 24, but the number and distribution are not limited and may be variously modified as necessary.

Figure 4A:
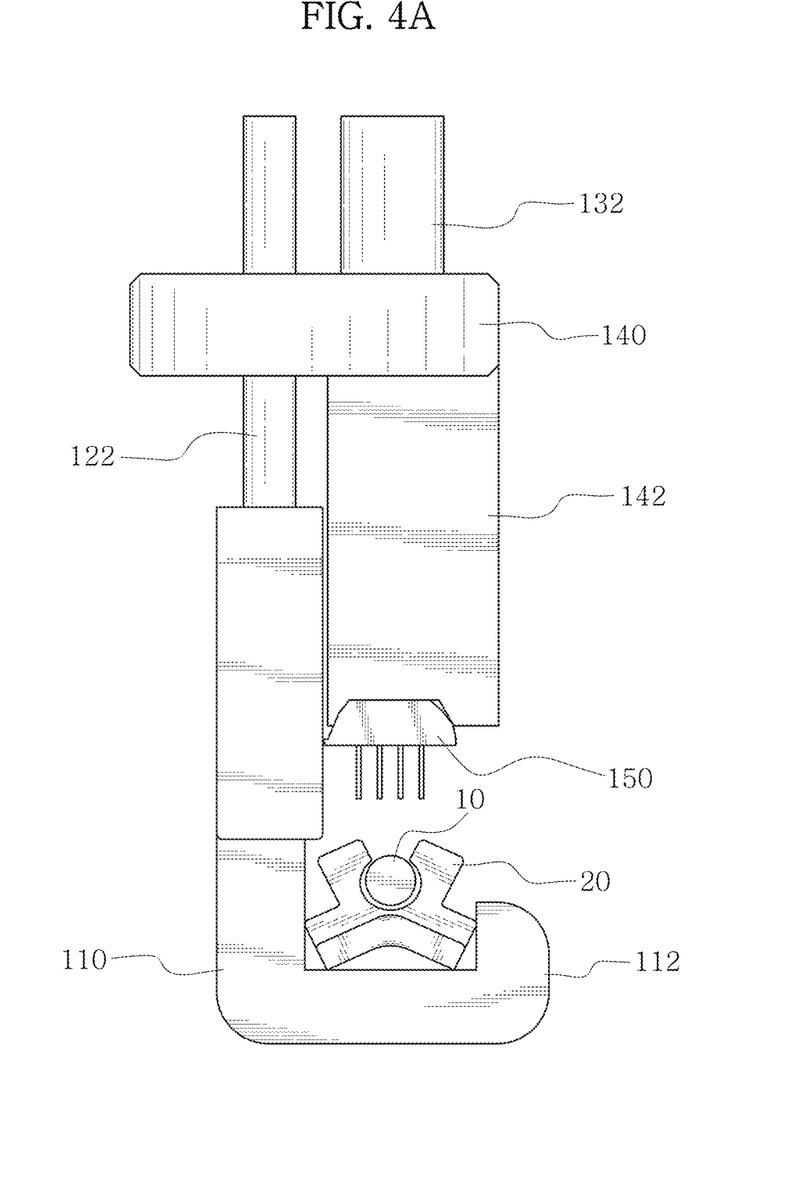
FIGS. 4A and 4B are a side view and a side projected view of an end of an apparatus for insertion of an electrode structure of a type of fixing the electrode structure by the magnetic force according to an embodiment of the present disclosure, respectively.
Figure 4B:
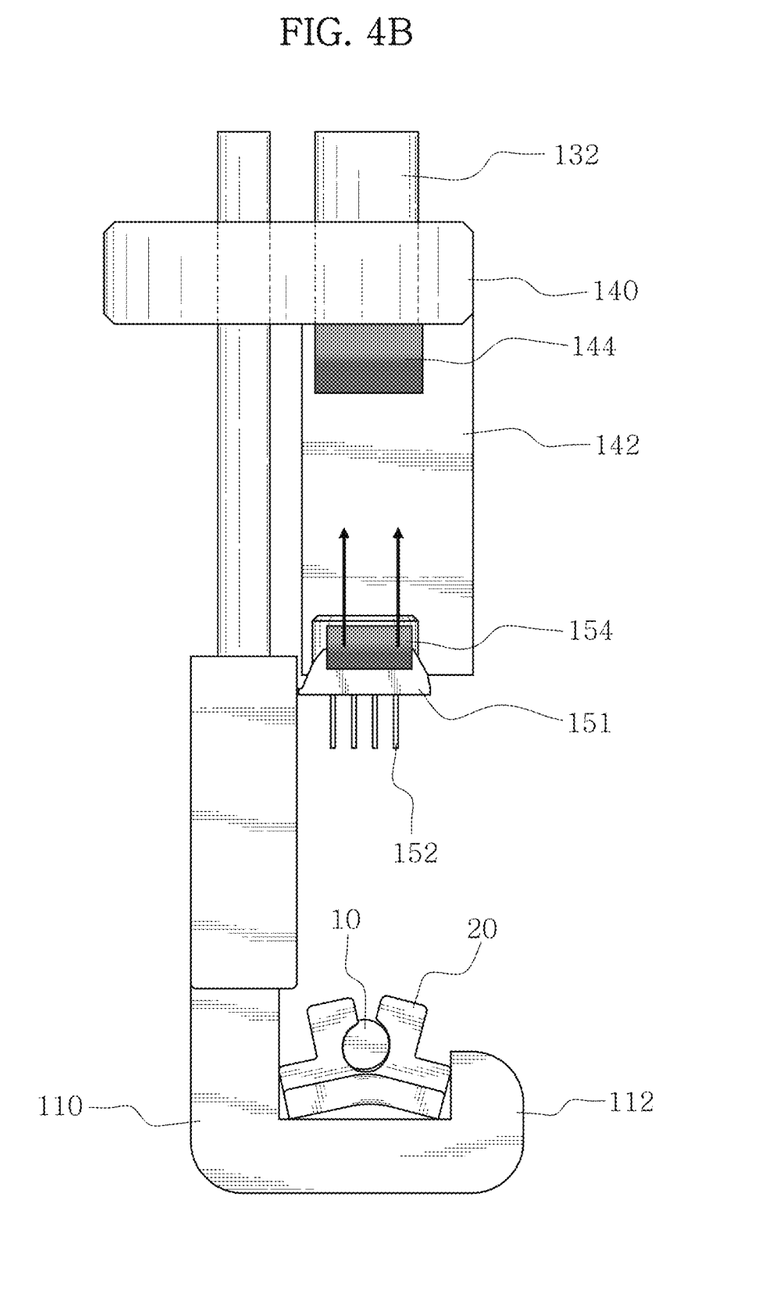

FIGS. 4A and 4B are a side view and a side projected view of an end of the apparatus 100 for insertion of an electrode structure of a type of fixing the electrode structure by the magnetic force according to an embodiment of the present disclosure, respectively. The electrode structure fixing part 140 of the apparatus 100 for insertion of an electrode structure of FIG. 1 may include a fixing part body 142 and a magnetic element 144.

As shown in FIG. 4A, the fixing part body 142 of a type of fixing the electrode structure 150 by the magnetic force according to an embodiment of the present disclosure may have an end structure of a shape for receiving the electrode structure 150 inside. For example, the electrode structure 150 that can be attached by the magnetic force is loaded at an end of a concave groove shape that is approximately equal or similar in size to the cross section of the electrode structure 150, and when the fixing part body 142 moves with the application of a predetermined magnitude or more of force to the pressing part 130, the electrode structure 150 loaded at the end moves toward the nerve cover fixing part 110 where the nerve 10 surrounded by the nerve cover 20 is placed.

As shown in FIG. 4B, the electrode structure fixing part 140 may include a magnetic element 144 having magnetic properties within the fixing part body 142, and the electrode structure 150 may include a magnetic element 154 having magnetic properties. The electrode structure 150 may be loaded in the electrode structure fixing part 140 by the action of an attractive force by the magnetic force between the magnetic element 144 of the electrode structure fixing part 140 and the magnetic element 154 of the electrode structure 150. According to an embodiment of the present disclosure, it is designed that a weak attractive force acts between the magnetic element 144 of the electrode structure fixing part 140 and the magnetic element 154 of the electrode structure 150, so after the electrode structure 150 is inserted into the nerve 10 surrounded by the nerve cover 20, the electrode structure 150 can be easily separated from the electrode structure fixing part 140 due to the attractive force that is smaller than friction with the nerve cover 20.

Although FIG. 4 shows only the apparatus 100 for insertion of an electrode structure of a type of fixing the electrode structure by the magnetic force, the type of fixing the electrode structure is not limited and may be modified in various forms. For example, the apparatus 100 for insertion of an electrode structure of a type of fixing the electrode structure by the negative pressure is possible. In this case, the center pole 132 connected with the electrode structure fixing part 140 may have a hollow center, and the electrode structure 150 may be fixed by the negative pressure through the suction pump connected through a side hole of the pressing part 130. In the case of the type of fixing the electrode structure 150 by the negative pressure, the electrode structure 150 may be inserted and fixed into the nerve 10 surrounded by the nerve cover 20 with the continuous application of a predetermined magnitude or more of force to the pressing part 130, and may be easily separated by removing the negative pressure.

Figure 5:
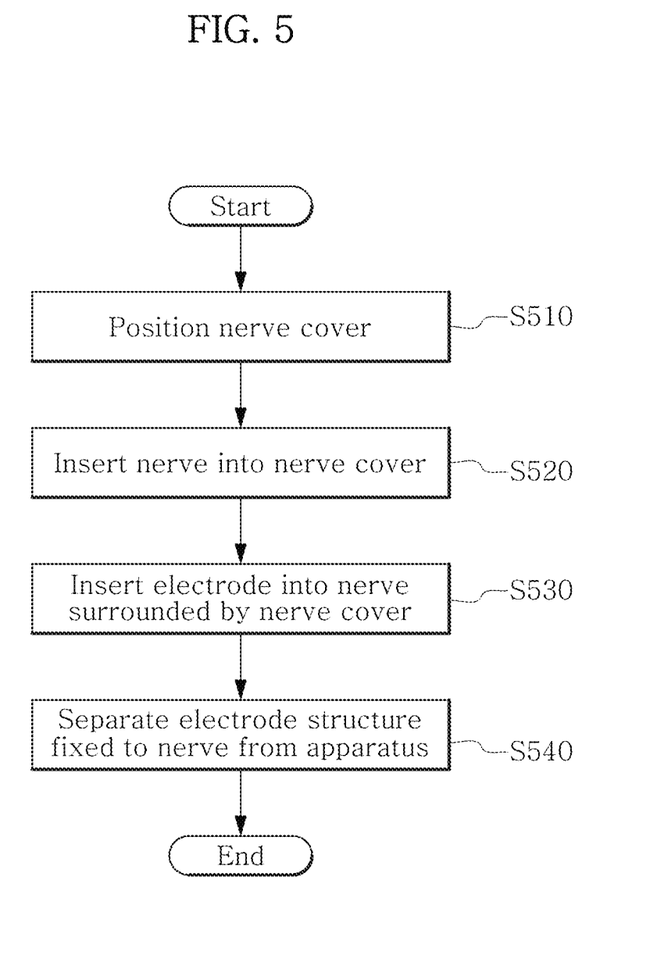
FIG. 5 is a flowchart of a process of inserting an electrode structure into a nerve using an apparatus for insertion of an electrode structure according to an embodiment of the present disclosure.

FIG. 5 is a flowchart of the process of inserting the electrode structure 150 into the nerve 10 using the apparatus 100 for insertion of an electrode structure according to an embodiment of the present disclosure.

Referring to FIG. 5, an embodiment of the method for inserting the electrode structure 150 into the nerve 10 using the apparatus 100 for insertion of an electrode structure includes positioning the nerve cover 20 in the nerve cover fixing part 110 (S510), inserting the nerve 10 into the nerve cover 20 (S520), inserting and fixing the electrode structure 150 into the nerve 10 surrounded by the nerve cover 20 (S530), and separating the electrode structure 150 fixed to the nerve 10 from the apparatus 100 for insertion of an electrode structure (S540).

First, the nerve cover 20 is positioned in the nerve cover fixing part 110 (S510). In other words, before the nerve 10 is positioned in the nerve cover fixing part 110, the nerve cover 20 is positioned and fixed to a protruding part 112 of the nerve cover fixing part 110. For example, the nerve cover 20 may have a structure in which the hole 23 in a circular horizontal cross section is placed on the straight line shaped flat base 24, and the hole 23 is open to top. The nerve cover 20 may be generally made of a polymer or silicone material having an elastic property, but may be modified to a shape or a material that can cover the nerve inside to prevent the nerve from being damaged.

Figure 6A:
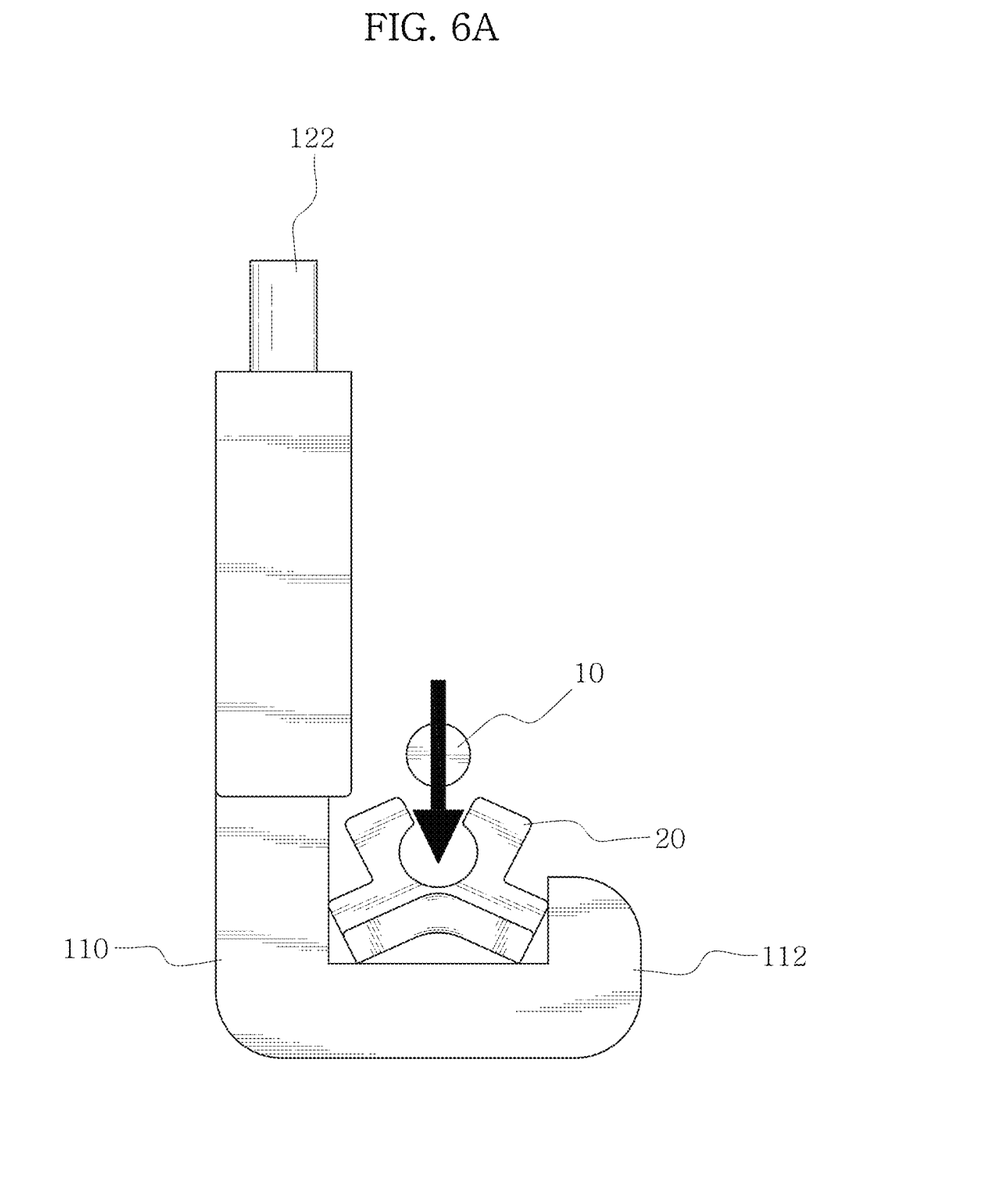
FIGS. 6A to 6E show a process of inserting and fixing an electrode structure into a nerve using an apparatus for insertion of an electrode structure according to an embodiment of the present disclosure.
Figure 6B:
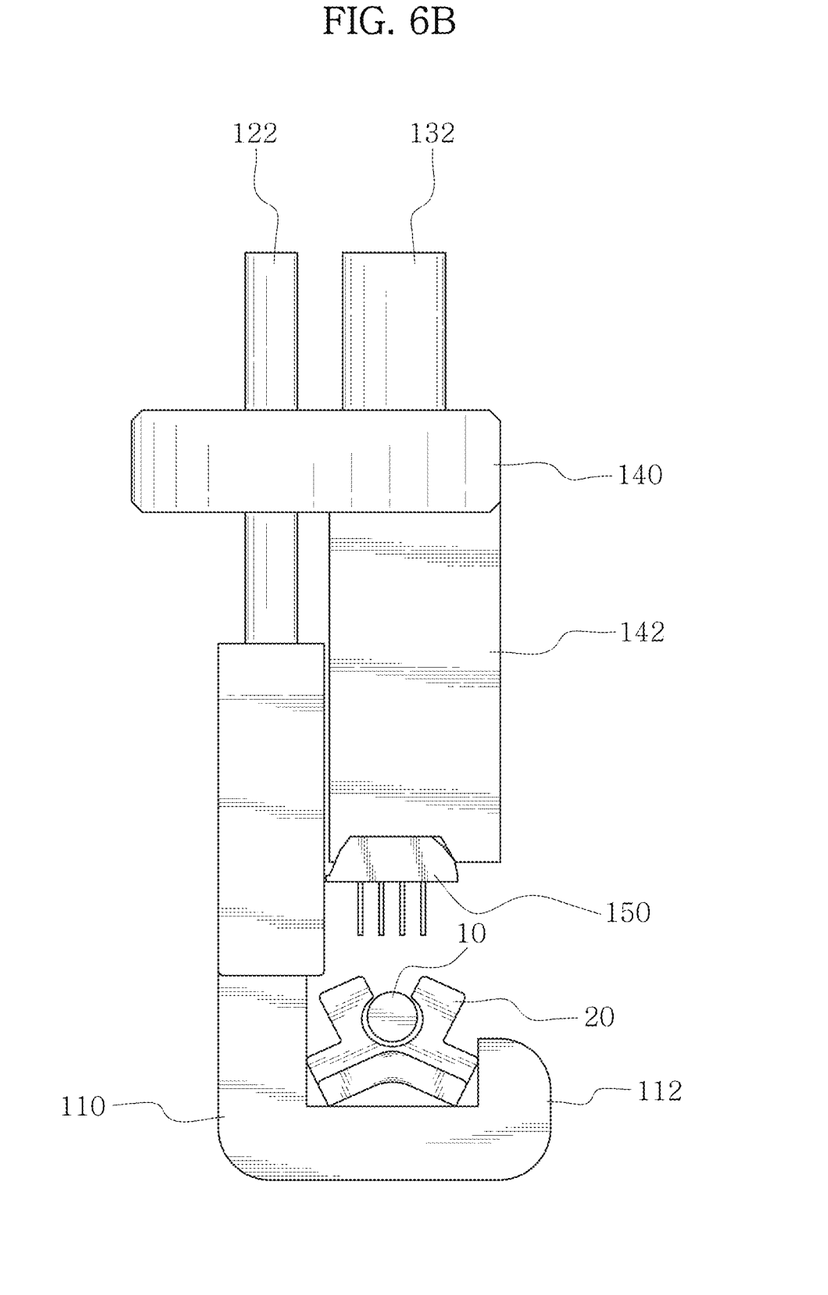
Figure 6C:
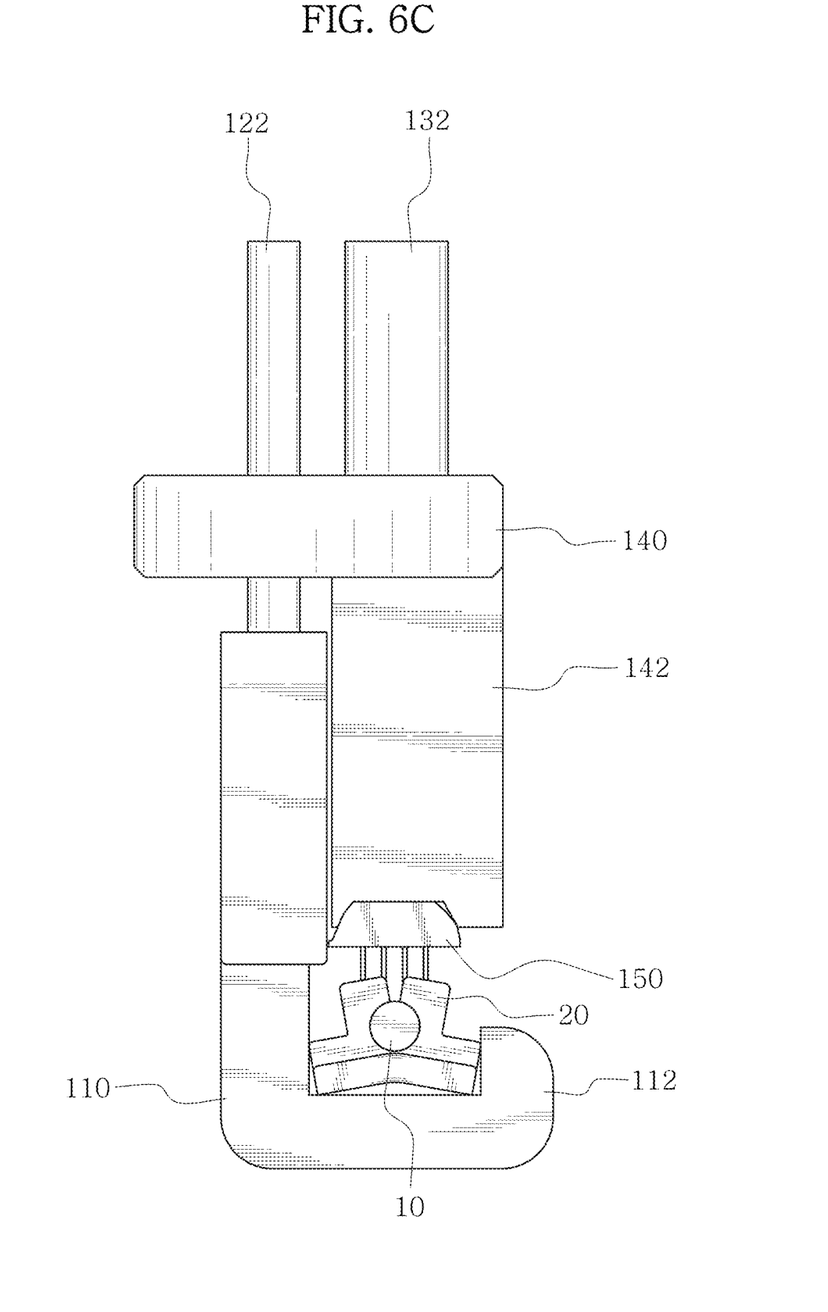
Figure 6D:
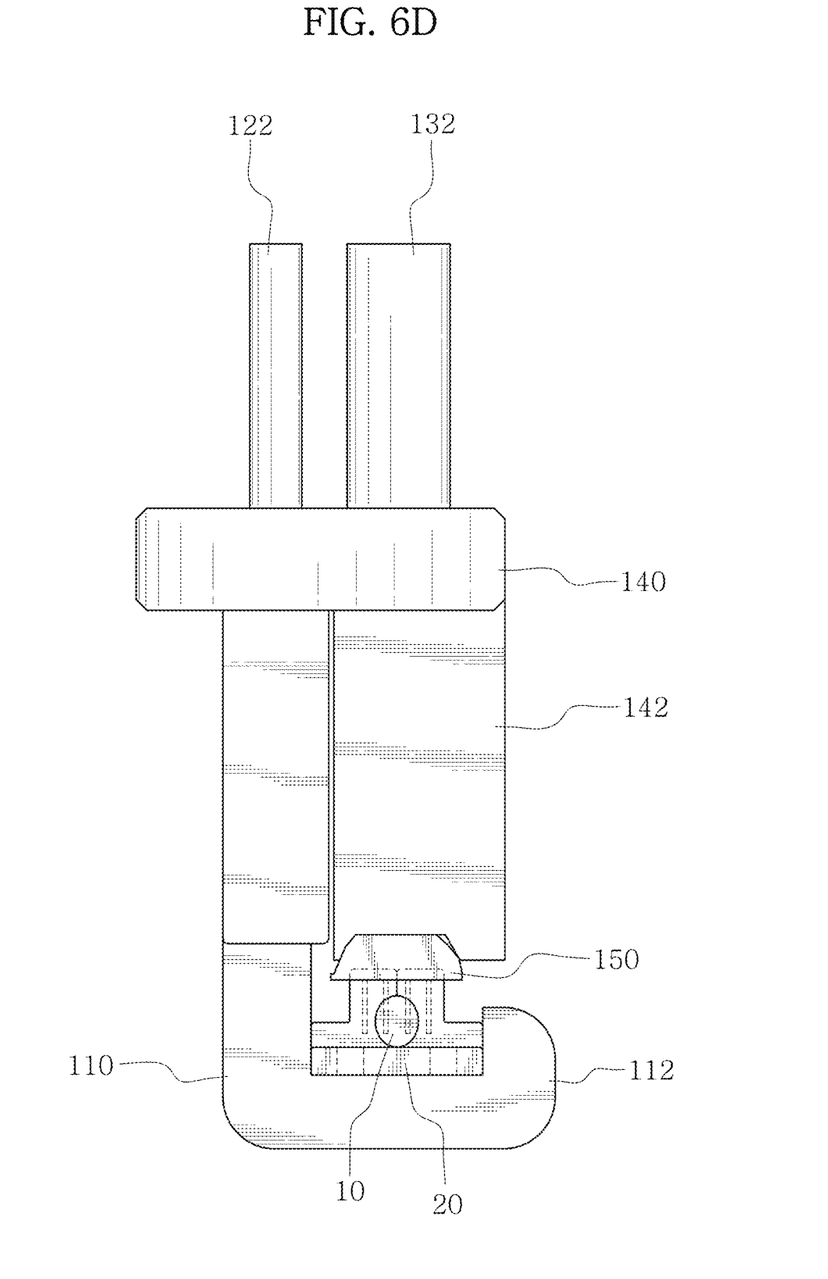

In detail, referring to FIG. 6A, the nerve cover 20 of an elastic material may have the bending of the base 24 into an arch shape such that the upper entrance of the hole 23 is open larger than the diameter of the nerve 10, and in this state, may be positioned and fixed to the nerve cover fixing part 110. The base 24 may be designed such that its width is equal or similar in size to the protruding length of the protruding part 112 of the nerve cover fixing part 110 to fix the nerve cover 20 to the nerve cover fixing part 110 when the base 24 is bent into an arch shape.

Subsequently, the nerve 10 is inserted into the nerve cover 20 (S520). In other words, the nerve 10 is positioned and fixed in the nerve cover 20 such that the nerve 10 part into which the electrode structure 150 is to be inserted is positioned in the protruding part 112 of the nerve cover fixing part 110. The nerve 10 part into which the electrode structure 150 is to be inserted may be seated in the nerve cover 20 and aligned on the same axis as the electrode structure fixing part 140. Through this, the electrode structure 150 may be inserted into a desired location of the nerve 10. The nerve cover 20 may be made of a soft material having appropriate elasticity for easily inserting the nerve 10 into the nerve cover 20 without damaging the nerve 10 when pushing the nerve 10 into the hole 23 through the open surface. For example, the nerve cover 20 may be made of a polymer or silicone material having an elastic property, but may be made of any material having an elastic property allowing it to restore to the original shape after the shape changes.

In detail, referring to FIGS. 6A and 6B, the base 24 of the nerve cover 20 may become an arch shape to expand the entrance size of the open hole 23 of the nerve cover 20, then the nerve cover 20 may be fixed to the protruding part 112 of the nerve cover fixing part 110 and the nerve 10 may be inserted into the hole 23 of the nerve cover 20. As shown in FIG. 6B, after the nerve 10 is inserted through the entrance of the hole 23 of the fixed nerve cover 20, when the pressure is applied to the base 24 bent into an arch shape, the arch shaped bottom may restore to some extent. As shown in FIG. 6C, when the pressure is continuously applied to insert the electrode structure 150, or the pressure is continuously applied to the base 24 in other forms, the arch shaped base 24 may easily restore to the shape of a straight line. When the base 24 restores to the shape of a straight line, the entrance returns to a much narrower state than the diameter of the nerve 10 surrounded within the hole 23, so the nerve 10 may be kept in fully surrounded state.

Subsequently, the electrode structure 150 is inserted and fixed into the nerve 10 surrounded by the nerve cover 20 (S530). When a greater force than the threshold enough to compress the elastic element 160 is applied to the pressing part 130, the fixing part body 142 of the electrode structure fixing part 140 moves down through the center pole 132 and the electrode structure 150 moves in proximity to the nerve 10 surrounded by the nerve cover 20. In this instance, the electrode structure 150 may be linearly inserted and fixed into the nerve 10 surrounded by the nerve cover 20 fixed to the nerve cover fixing part 110 on the same axis as the electrode structure fixing part 140.

In detail, referring to FIGS. 6C and 6D, the force may be applied to the pressing part 130 to position the electrode structure 150 in proximity to the nerve 10 positioned in the nerve cover fixing part 110, and the force may be continuously applied to the pressing part 130 to stably insert the electrode structure 150 into the nerve 10 surrounded by the nerve cover 20. When the nerve 10 is inserted into the hole 23 but the base 24 is not fully extended in the shape of a straight line, the base 24 is restored to the shape of a straight line by the downward pressure for inserting the electrode structure 150, and the nerve 10 is fully surrounded within the hole 23 of the nerve cover 20. In this state, the electrode structure 150 may be stably inserted and fixed in the form of a complex structure of the nerve—the nerve cover—the electrode structure.

Finally, the electrode structure 150 fixed to the nerve 10 is separated from the apparatus 100 for insertion of an electrode structure (S540). When the force applied to the pressing part 130 is removed, the electrode structure fixing part 140 is prone to return to the original position by the restoring force of the elastic element 160. In this instance, when it is designed that friction between the nerve cover 20 made of a soft material and the electrode structure 150 is greater than the magnetic force for fixing the electrode structure 150 to the electrode structure fixing part 140, the electrode structure 150 fixed by the magnetic force is easily separated from the electrode structure fixing part 140. According to another embodiment, it may be designed that the electrode structure 150 is separated from the electrode structure fixing part 140 by the action of a repulsive force between the magnetic elements 144, 154 by changing the direction of the magnetic force, then the electrode structure fixing part 140 returns to the original position. When the electrode structure 150 is separated from the electrode structure fixing part 140, the nerve—the nerve cover—the electrode structure fixed with the electrode structure 150 is completely separated from the apparatus 100 for insertion of an electrode structure, and the process of inserting the electrode structure 150 into the nerve 10 is completed.

Figure 6E:
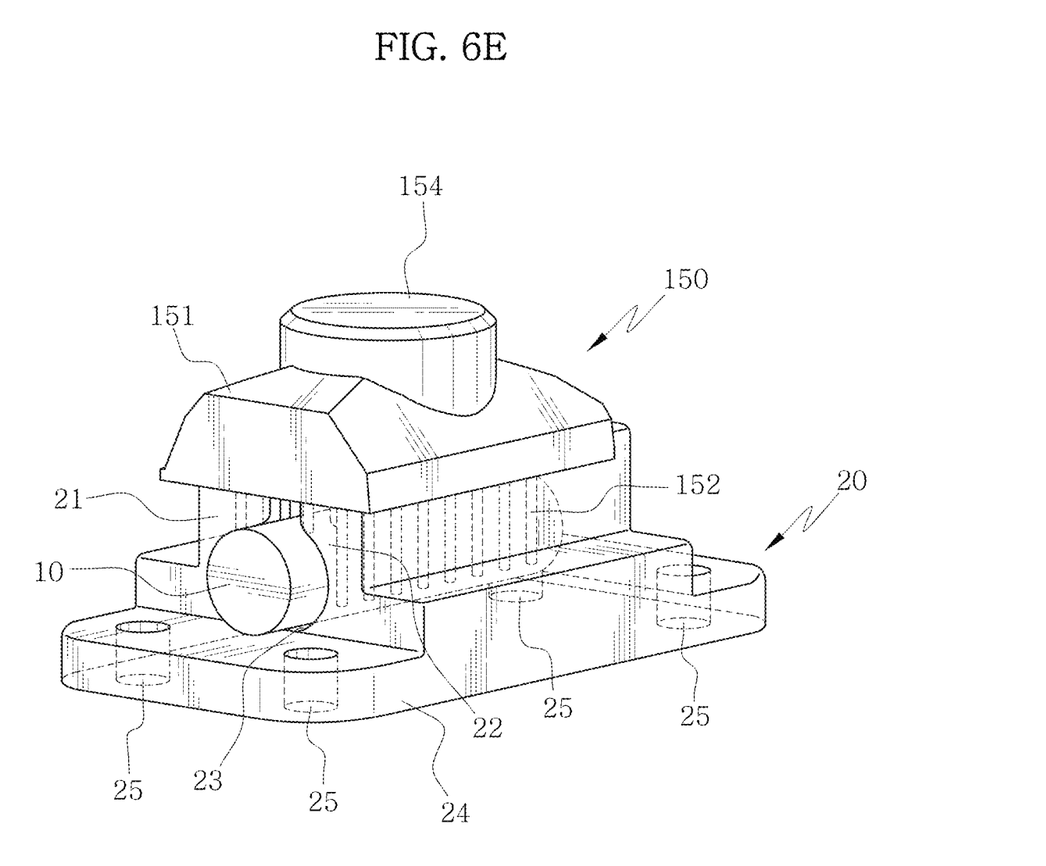

In detail, referring to FIG. 6E, when the force applied to the pressing part 130 is removed, the electrode structure fixing part 140 may return to the original position by the restoring force of the elastic element 160, and the electrode structure 150 fixed by the magnetic force may be separated from the electrode structure fixing part 140. Through this, the electrode structure 150 fixed with the nerve 10 surrounded by the nerve cover 20 may be separated from the apparatus 100 for insertion of an electrode structure.

According to an embodiment of the present disclosure, referring to FIG. 6E, there is an example of a three-dimensional multielectrode array 150 inserted and fixed into the nerve 10 using the apparatus 100 for insertion of an electrode structure. The three-dimensional multielectrode array 150 may have an asymmetrical body 151 with one wide and flat surface and the other surface that becomes narrower in a curve shape, and may include a plurality of probes 152 on the wide and flat surface of the body 151. A magnetic element 154 may be provided on the other surface to load the electrode structure 150 on the electrode structure fixing part 140 by the magnetic force.

As described above, when the process of inserting the electrode structure 150 into the nerve 10 through the nerve cover 20 is completed, as shown in FIG. 6E, it is possible to deliver electrical stimulation to the nerve and measure electrical signals of neural activity through the electrode structure 150 fixed more firmly by friction with the nerve cover 20 surrounding the nerve 10.

In the specific embodiments described above, elements included herein are expressed in singular or plural forms according to the specific embodiments presented herein. However, singular or plural forms are selected suitably for the presented situation for convenience of description, the disclosed embodiments are not limited to the singular or plural elements, and elements expressed in plural form may be singular elements, or elements expressed in singular form may be plural elements.

While specific embodiments have been described in the detailed description, it is obvious that many modifications may be made without departing from the technical spirit included in various embodiments. Therefore, the scope of the present disclosure should not be limited to the disclosed embodiments, and should be defined by the appended claims and equivalent to the claims.

[Detailed Description of Main Elements]

| | |
|---|---|
| 10: Nerve | 20: Nerve cover |
| 21, 22: Cover | 23: Hole |
| 24: Base | 25: Fixing hole |
| 100: Apparatus for insertion of an electrode structure | |
| 110: Nerve cover fixing part | |
| 112: Protruding part | 120: Body |
| 122: Sliding element | 124: Elastic press plate |
| 126: Support | 130: Pressing part |
| 132: Center pole | 140: Electrode structure fixing part |
| 142: Fixing part body | 144: Magnetic element |
| 150: Electrode structure | 151: Body |
| 152: Probe | 154: Magnetic element |
| 160: Elastic element | |

What is claimed is:

1. An apparatus for insertion of an electrode structure for inserting an electrode structure into a nerve within a living body tissue, comprising:
    a nerve cover fixing part which fixes a nerve cover, the nerve cover comprising
        a base of a flat plate shape, and
        a pair of covers protruding upward from the base to form a hole for receiving a nerve, with one end attached to the base and another end spaced apart from the one end,
        wherein
            an inner surface of the hole has a substantially cylindrical shape,
            the base is wider than the pair of covers, and
            when the base is bent in an arch shape when viewed from a side, a spacing between the pair of covers is expanded; and
    an electrode structure fixing part in which the electrode structure is mounted, and which linearly moves the mounted electrode structure in an insertion direction to insert the electrode structure into the nerve surrounded by the nerve cover;
    wherein the nerve cover fixing part is arranged opposite to the electrode structure fixing part and has a groove structure, the groove structure having an opening for accommodating the nerve cover and a protruding part bordering the opening on one side; and wherein when the nerve cover is accommodated in the opening of the groove structure, the base is bent in the arch shape to form the expanded spacing between the pair of covers by pressure applied to edges of the base extending beyond the pair of covers by the protruding part on the one side and by a part of the groove structure on another side.

2. The apparatus for insertion of an electrode structure according to claim 1, wherein the base includes one or more fixing holes that are sutured with a string to fix the nerve cover to the living body tissue.

3. The apparatus for insertion of an electrode structure according to claim 1, further comprising:

a pressing part which applies a force to the electrode structure fixing part to move the electrode structure in the insertion direction.

4. The apparatus for insertion of an electrode structure according to claim 3, wherein the electrode structure fixing part is connected with the pressing part by a central pole, and the force applied to the pressing part is transferred to the electrode structure fixing part through the center pole.

5. The apparatus for insertion of an electrode structure according to claim 4, further comprising:

an elastic element disposed between an elastic press plate attached to the center pole and a support through which the center pole moves, wherein the elastic element is compressed against the support as the center pole moves when a force above a threshold is applied to the pressing part.

6. The apparatus for insertion of an electrode structure according to claim 1, wherein the electrode structure fixing part includes a magnetic element inside, and the electrode structure includes a magnetic element on top, and is fixed to the electrode structure fixing part by a magnetic force between the magnetic elements.

7. The apparatus for insertion of an electrode structure according to claim 1, wherein the electrode structure is fixed to the electrode structure fixing part by a negative pressure, and when the negative pressure is removed, is separated from the electrode structure fixing part.

8. The apparatus for insertion of an electrode structure according to claim 1, wherein the nerve cover is made of a soft material having an elastic property, and while the electrode structure is inserted into the nerve surrounded by the nerve cover through the linear movement, the base bent into the arch shape is restored to a flat shape and the expanded spacing between the pair of covers is restored to an original spacing.

9. The apparatus for insertion of an electrode structure according to claim 3, further comprising:

a high frequency vibration motor attached to the pressing part or the electrode structure fixing part, wherein the high frequency vibration motor reduces a pressure and friction applied to the living body tissue while the electrode structure is inserted into the nerve.

10. The apparatus for insertion of an electrode structure according to claim 1, further comprising:

the electrode structure;

wherein the electrode structure comprises a three-dimensional multielectrode array.

11. The apparatus for insertion of an electrode structure according to claim 10, wherein the three-dimensional multielectrode array has an asymmetrical body with one wide and flat surface and another surface that becomes narrower in a curve shape, and includes a plurality of probes on the wide and flat surface of the body; and wherein when the nerve cover is accommodated in the opening of the groove structure and surrounds the nerve, the plurality of probes penetrate the nerve cover.

* * * * *